United States Patent [19]

Flitsch et al.

[11] Patent Number: 6,100,074

[45] Date of Patent: Aug. 8, 2000

[54] MUTANT MONO-OXYGENASE CYTOCHROME P-450 $_{CAM}$

[75] Inventors: Sabine Lahja Flitsch, Edinburgh; Darren Paul Nickerson; Luet-Lok Wong, both of Oxford, all of United Kingdom

[73] Assignee: BG plc, Reading, United Kingdom

[21] Appl. No.: 08/860,571

[22] PCT Filed: Nov. 2, 1995

[86] PCT No.: PCT/GB95/02588

§ 371 Date: Jan. 27, 1998

§ 102(e) Date: Jan. 27, 1998

[87] PCT Pub. No.: WO96/14419

PCT Pub. Date: May 17, 1996

[30] Foreign Application Priority Data

Nov. 3, 1994 [GB] United Kingdom .................. 9422205

[51] Int. Cl.$^7$ .............................. C12N 9/02; C12P 7/00; C12P 21/06; C07K 1/00

[52] U.S. Cl. ..................... 435/189; 435/69.1; 435/132; 530/402

[58] Field of Search ................. 435/172.3, 189, 435/68.1, 69.1, 132; 530/402, 808; 424/94.4

[56] References Cited

PUBLICATIONS

Richardson et al. "Alterations of the regiospecificity of progesterone metabolism by the mutagenesis of two key amino acid residues in rabbit cytochrome P450 2C3v," J. Biol. Chem. (1994) 269(39): 23937–43.

Di Primo et al. "Mutagenesis of a single hydrogen bond in cytochrome P450 alters cation binding and heme solvation," J. Biol. Chem. (1990) 265(10): 5361–63.

Atkins et al. "The roles of active site hydrogen bonding in cytochrome P450cam as revealed by site–directed mutagenesis," J. Biol. Chem. (1988) 263(35): 18842–49.

William M. Atkins and Stephan G. Sligar, "Molecular Recognition in Cytochrome P–450: Alteration of Regioselective Alkane Hydroxylation via Protein Engineering," J. Am. Chem. Soc., 1989, 111(7). 2715–2717.

*Primary Examiner*—Jean C. Witz
*Assistant Examiner*—Susan Hanley
*Attorney, Agent, or Firm*—William H. Holt

[57] ABSTRACT

A mutant of the mono-oxygenase cytochrome P-450$_{cam}$ in which the tyrosine residue at position 96 and/or the cysteine residue at positon 334 is replaced by the residue of any amino acid except phenylalanine.

11 Claims, 2 Drawing Sheets

MUTANT MONO-OXYGENASE CYTOCHROME P-450 $_{CAM}$

This application is the National Stage of International Application No. PCT/GB95/02588, filed Nov. 2, 1995.

The present invention relates to a mutant of the mono-oxygenase cytochrome P-450$_{cam}$ and method of oxidising certain organic compounds with the mutant.

BACKGROUND OF THE INVENTION

Mono-oxygenases catalyse the selective oxidation of non-functionalised hydrocarbons using oxygen[1], and are therefore of great interest for potential use in organic synthesis. However, progress in this area has been hampered by the difficulty in isolating sufficient quantities of enzyme and the associated electron-transfer proteins. Despite the availability of amino acid sequences of more than 150 different cytochrome P-450 mono-oxygenases, to date structural data of only three are available[2,3,4], and few have been successfully over-expressed in bacterial systems[5].

One cytochrome P-450 mono-oxygenase, which is soluble and can be expressed in sufficient quantities, is the highly specific P-450$_{cam}$ from P.putida which catalyses the regio- and stereo-selective hydroxylation of camphor (1) to 5-exo-hydroxycamphor[6]. The high resolution crystal structure of P-450$_{cam}$ has been determined[2], and since the mechanism of action of this bacterial enzyme is believed to be very similar to that of its mammalian counterparts, it has been used as a framework on which models of mammalian enzymes are based.

The nucleotide sequence and corresponding amino acid sequence of P-450$_{cam}$ have been described[5]. The location of an active site of the enzyme is known and structure-function relationships have been investigated[13, 14]. Mutants of P-450$_{cam}$ have been described, at the 101 and 185 and 247 positions[15], and at the 87 position[16]. A mutant in which tyrosine 96 has been changed to phenyl alanine-96 has been described[12,17,18]. But in all these cases the papers report effects of the mutations on the mechanisms of known oxidation reactions. There is no teaching or suggestion that mutation might be used to provide biocatalysts for oxidation of different substrates.

SUMMARY OF THE INVENTION

In an attempt to find new biocatalysts, we have initiated a project which aims to redesign the active site of P-450$_{cam}$, such that it is able to carry out specific oxidations of organic molecules which are not substrates for the wild-type protein. Our initial aim was to incorporate an "aromatic pocket" into the P-450$_{cam}$ active site, which would encourage the binding of substrates containing aromatic side-chains.

In addition, a surface residue remote from the active site was identified (cysteine-334) with effects on protein handling and stability. The cysteine is responsible for unwanted dimerisation of the protein during purification and an alanine residue was therefore substituted for the cysteine in order to improve both of these properties.

The three dimensional structure of P-450$_{cam}$ shows the active site to provide close van der Waals contact with the hydrophobic groups of camphor as shown in FIG. 1. Three aromatic residues (Y96, F87 and F98) are grouped together and line the substrate binding pocket, with a hydrogen bond between tyrosine 96 and the camphor carbonyl oxygen maintaining the substrate in the correct orientation to ensure the regio-and stereo-specificity of the reaction. Replacement of any of these aromatic residues with a smaller, hydrophobic non-aromatic side-chain could provide the desired "aromatic pocket".

Molecular modelling was used to investigate the likely effects of point mutations to the three aromatic residues. The program GRID[7] was used to calculate an energy of interaction between an aromatic probe and possible mutants of cytochrome P-450$_{cam}$ where these residues were changed to alanine (F87A, Y96A and F98A). The results were then examined graphically using the molecular modelling package Quanta[8].

The mutant F98A appeared to have the strongest binding interaction within the active site cavity accessible to the aromatic probe, with that of Y96A being slightly smaller, and that of F87A being substantially less. It was decided in the first instance to mutate tyrosine 96 to alanine as it is more central to the binding pocket, whereas phenylalanine 98 is in a groove to one side. Also, removal of tyrosine 96 should decrease the specificity of the enzyme towards camphor due to the loss of hydrogen bonding to the substrate.

According to one aspect of the present invention a mutant of the mono-oxygenase cytochrome P-450$_{cam}$ is provided in which the tyrosine residue at position 96 and/or the cysteine residue at position 334 is replaced by the residue of any amino acid except phenylalanine.

According to another aspect of the present invention a mutant of the mono-oxygenase cytochrome P-450$_{cam}$ is provided in which the tyrosine residue at position 96 and/or the cysteine residue at position 334 is replaced by another amino acid residue, which mutant has the property of catalysing the oxidation of any one of the following:- polycyclic aromatic hydrocarbons, linear or branched alkanes, diphenyl and biphenyl compounds including halogenated variants of such compounds and halogenated hydrocarbons.

According to yet another aspect of the present invention a method is provided of oxidising a compound selected from a polycyclic aromatic hydrocarbon, a linear or branched alkane, a diphenyl or biphenyl compound including a halogenated variant of such a compound or a halogenated hydrocarbon, the method comprising contacting the selected one of the compounds under oxidising conditions with mono-oxygenase cytochrome P-450$_{cam}$ in which the tyrosine residue at position 96 and/or the cysteine residue at position 334 is replaced by another amino acid residue.

Preferably the amino acid is selected from any one of the following: alanine, arginine, asparagine, aspartic acid, cysteine, glutamic acid, glutamine, glycine, histidine, isoleucine, leucine, lysine, methionine, proline, serine, threonine, tryptophan, tyrosine and valine except that in the case of the tyrosine residue at position 96, the amino acid is not tyrosine and in the case of the cysteine residue at position 334, the amino acid is not cysteine.

The amino acid which replaces tyrosine at position 96 is conveniently one of the small hydrophobic amino acids, e.g. alanine, glycine, valine, leucine or isoleucine, with alanine being preferred as exemplified below.

Alternatively the amino acid replacing tyrosine at position 96 may be one of the charged amino acids, e.g. a negatively charged acid such as aspartic acid or glutamic acid for hydrogen bonding to a positively charged substrate; or a positively charged compound such a lysine, arginine or histidine for hydrogen bonding to a negatively charged substrate which are not members of the camphor family.

The mutation at position 96 is believed to be the key which enables the mutant enzymes to catalyse the oxidation of a relatively wide range of organic substrates. Other amino acids adjacent to the active site of the enzyme may also be mutated in order to change the shape and specificity of the active site. These other amino acids include those at positions 87, 98, 185, 244, 247, 295 and 297. It is envisaged that the amino acid at one or more of these positions may be replaced by: a small hydrophobic amino acid so as to enlarge the active site; or a large hydrophobic amino acid so as to reduce the size of the active site; or by an amino acid having an aromatic ring to bond to a corresponding aromatic ring of a substrate.

Regarding the oxidising reactions, the conditions are described in the literature references attached. The enzyme system typically includes putidaredoxin and putidaredoxin reductase together with NADH as co-factors in addition to the mutant enzyme. Various classes of organic compounds are envisaged:

i) The organic compound is an aromatic compound, either a hydrocarbon or a compound used under conditions in which it does not inactivate or denature the enzyme. Since the mutation has been effected with a view to creating an aromatic-binding pocket in the surface of the enzyme, the mutant enzyme is capable of catalysing oxidation of a wide variety of aromatic compounds. Oxidation of example aromatic and polyaromatic compounds is demonstrated in the experimental section below and is believed very surprising given that the wild-type enzyme catalyses the oxidisation of only members of the camphor family.

ii) The organic compound may be a hydrocarbon, e.g. aliphatic or alicyclic, carrying a functional group. An aromatic protective group is added to the functional group prior to the oxidation reaction and removed from the functional group after the oxidation reaction. A suitable aromatic group is a phenyl group. The aromatic protection group is expected to hold the substrate in place. Thus the protecting group serves two purposes: firstly it makes the substrate more hydrophobic and hence increases binding to the hydrophobic enzyme pocket; secondly it holds the substrate in place at the active site. Thus, with the correct aromatic protection group, both regio-and stereo-selective hydroxylation of the substrate may be achieved. The example of cyclohexylbenzene is described in the experimental section below.

Examples of monofunctionalised hydrocarbons are cyclohexyl, cyclopentyl and alkyl derivatives (Scheme 1). The oxidation products of these compounds are valuable starting materials for organic synthesis, particularly when produced in a homochiral form. A range of aromatic protecting groups are envisaged, e.g. benzyl or naphtyl ethers and benzoyl or naphthoyl esters and amides (Scheme 1). Of interest are also benzoxazole groups as carboxyl protecting groups and N-benyl oxazolidine groups as aldehyde protecting groups. Both can be easily cleaved after the enzymatic oxidation and have previously been described in the literature for the microbial oxidations of aldehydes and acids.

iii) The organic compound is a C5 to C12 aliphatic or alicyclic hydrocarbon. Oxidation of cyclohexane and linear hydrocarbons is demonstrated in the experimental section below and once again it is believed quite surprising given that the wild-type enzyme catalyses the oxidation of only members of the camphor family.

iv) The organic compound is a halogenated aliphatic or alicyclic hydrocarbon. Oxidation of lindane (hexachlorocyclohexane) is also described below.

Figure 1:
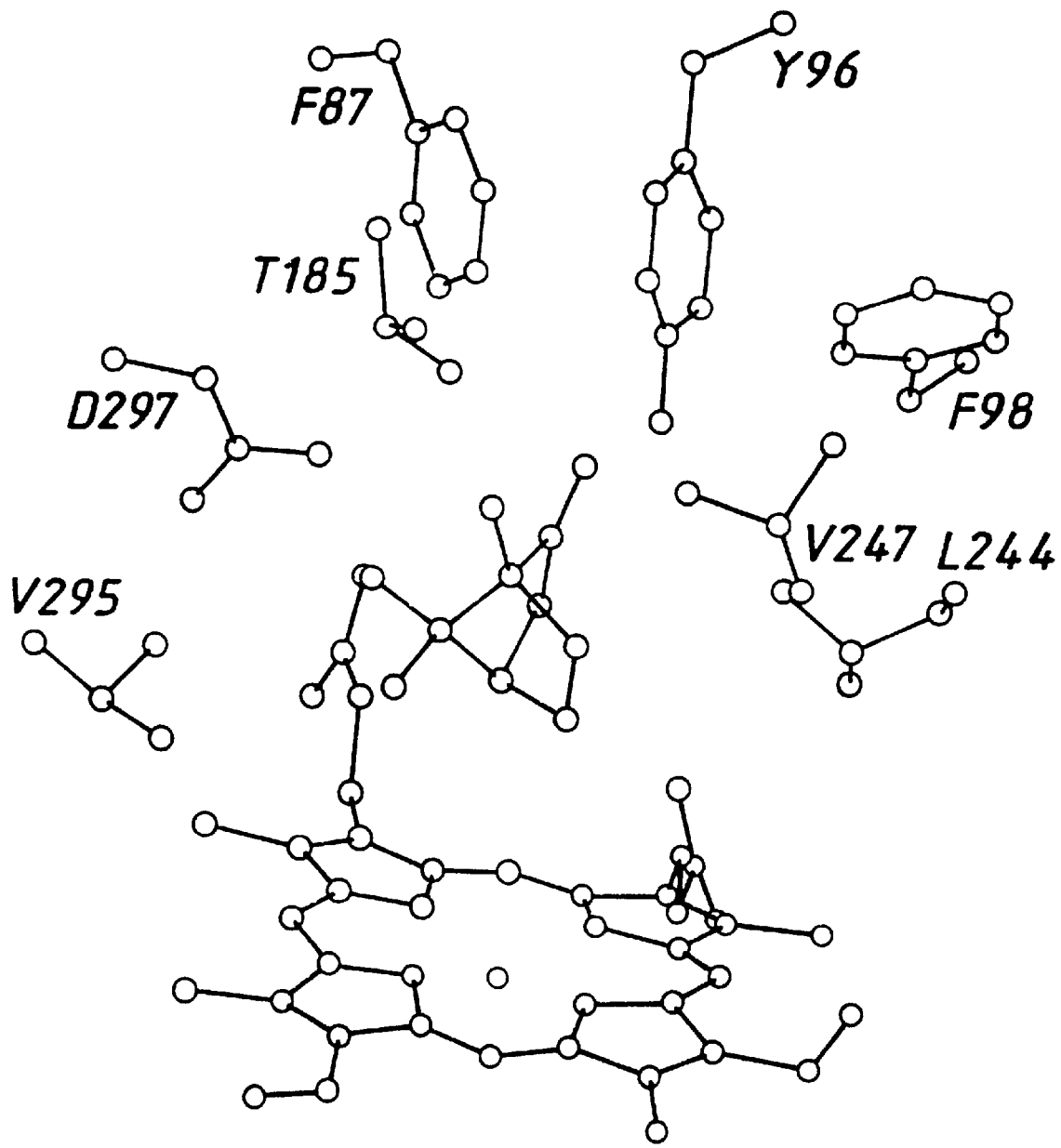
FIG. 1 is a showing that the three dimensional structure of P-450$_{cam}$ shows the active site to provide close van der Waals contact with the hydrophobic groups of camphor.

Based on the above considerations, mutant proteins were constructed which contained alanine, lysine, valine, or phenylalanine instead of tyrosine at position 96 (Y96). Additional mutants were constructed in which these active site replacements were combined with the surface mutation of cysteine at position 334 to alanine. Lastly several active site mutations and the surface mutation were combined in one protein to constitute a multiple mutant enzyme. The genes encoding cytochrome P-450$_{cam}$, and its natural electron-transfer partners puridaredoxin and putidaredoxin reductase, were amplified from the total cellular DNA of P. Putida using the polymerise chain reaction (PCR). The expression vector/E. coli host combinations employed were pRH1091[9] in strain JM109 for P-450$_{cam}$, pUC 118 in strain JM109 for putidaredoxin, and pGLW11 in strain DH5$^{oc}$ for putidaredoxin reductase. Oligonucleotide-directed site-specific mutagenesis was carried out using an M13mp19 subclone by the method of Zoller and Smith[10], and mutant selection was by the method of Kunkel[11].

The mutant Y96A was shown to catalyse the hydroxylation of camphor (1), although compared to the wild-type enzyme the reaction was less selective, similar to that reported for the mutant Y96F[12]. This decrease in selectivity can be attributed to the loss of the hydrogen bond between Y96 and camphor. The properties of wild-type and Y96A proteins were further investigated with a variety of binding and activity assays.

Binding of potential substrates was investigated by spectroscopic methods. The wild-types enzyme in the absence of substrate is in the 6-co-ordinated, low-spin form with a weakly bound water occupying the sixth co-ordination site, and shows a characteristic Soret maximum at 391 nm. Binding of the substrate analogues adamantanone (2), adamantane (3) and norbornane (4) also fully converted the haem to the high-spin form. However, diphenylmethane (5) did not give a shift in the absorption spectrum.

The Y96A mutant, while giving the same results for compounds (3) and (4), was not fully converted to the high-spin form even when (1) and (2) were added in excess. Most interestingly however, and in contrast to the wild-type, Y96A showed partial conversion to the haem to the high-speed form with diphenylmethane, indicating binding of this compound to the mutant protein.

As expected, the dissociation constants ($K_{app}$) for camphor and adamantanone are increased in Y96A. On the other hand, the $K_{app}$ values for the hydrophobic substrates adamantane and norbornane are reduced, indicating that the enzyme pocket has become more selective for hydrophobic substrates. The greatest change in binding was obtained with diphenylmethane, which bound poorly to wild-type protein, but showed greatly enhanced affinity for the Y96A mutant (Table 1).

Once binding of diphenylmethane by the Y96A protein had been established, catalytic substrate turnover was investigated. The mutant protein was reconstituted with putidaredoxin and putidaredoxin reductase. Diphenylmethane (5) was added and the mixture was incubated with NADH and oxygen.

A solution containing 10 μM putidaredoxin, 2 μM putidaredoxin reductase, 1 μM cytochrome P-450$_{cam}$ monoxygenase (wild-type or mutant) and 1 mM diphenylmethane in 100 mM KCl, 20 mM KH$_2$PO$_4$pH7.4 was preincubated at 25° C. in a shaker for 5 min. The enzymatic reaction was initiated by firstly adding NADH to a total concentration of 2 mM. Further four aliquots of NADH (to increase the NADH concentration by 1 mM each time) were added in intervals of 5 min and the reaction quenched after 30 min by adding 0.5 ml chloroform. The chloroform layer was analysed by gas chromatography.

Figure 2:
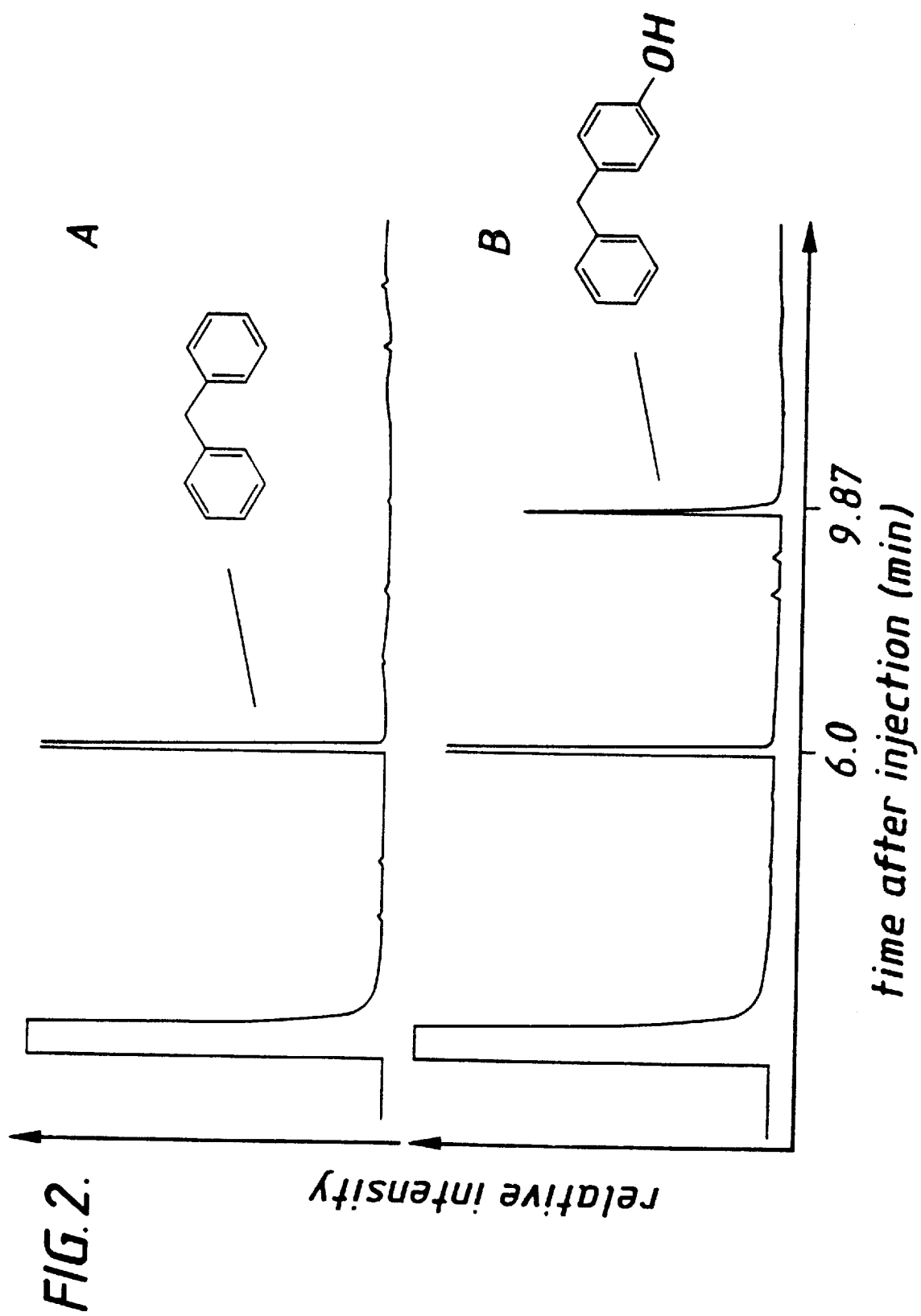
FIG. 2 is a gas chromatograph of diphenylmethane (A) and hydroxylated product formed following incubation with P-450$_{cam}$ Y96A mutant.

Organic extracts of the crude incubation mixture were analysed by gas chromatography. Only one major new peak was detected by GC (see FIG. 2), which had the same retention time as an authentic sample of para-hydroxydiphenylmethane (6). The other aromatic hydroxylation products, the ortho and meta isomers, had different retention times. Further confirmation of the identity of the product as structure (6) was provided by mass spectrometry, which gave the correct mass peak at 184.

Using the above experimental techniques, the inventors have investigated a considerable number of organic compounds as substrates for both the wild-type P-450$_{cam}$ enzyme and also the mutant version Y96A. Further work has included mutants designated Y96V; Y96L; Y96F; C334A; the combined mutant F87A, Y96G, F193A and the combined active site and surface mutants of Y96A, C334A; Y96V, C334A; Y96L, C334A; Y96F, C334A; F87A, Y96G, F193A, C334A.

The results for Y96A are set out in Table 2, in which structurally related molecules are grouped together. Those substrates where oxidation has been demonstrated by means of NADH turnover are marked with a + sign.

Spin high/low: numbers shows the percentage of P-450 (OD$_{417}$ 0.2-0.4) converted from the low- to high-spin equilibrium state in the presence of 200 μM test compound, in phosphate buffer (40 mM phosphate, 68 mM potassium, pH 7.4). Spin state equilibrium is assessed with a UV/vis spectrophotometer: low spin at OD$_{417}$ and high spin at OD392 nd; not done.

Vs DTT: numbers show the percentage displacement of DTT (200 μM) bound to P-450 by competition with test compounds (200 μM) in phosphate buffer. DTT binding to P-450 results in absorbance peaks at OD374 and OD$_{461}$, so displacement is measured with a UV/vis spectrophotometer.

Examples are included in Table 2(a) to 2(h) for each class of compounds identified in points (i) to (iv) above.

Reaction products for some substrate compounds have been purified by high performance liquid chromatography and identified by mass spectroscopy, nuclear magnetic resonance, and/or co-elution. Table 3 details the NADH consumption for oxidation of small linear, branched and cyclic hydrocarbons by the mutant Y96A, C334A. Table 4(a) to 4(h) details the product distributions for mutant and substrate combinations where this has been elucidated to date.

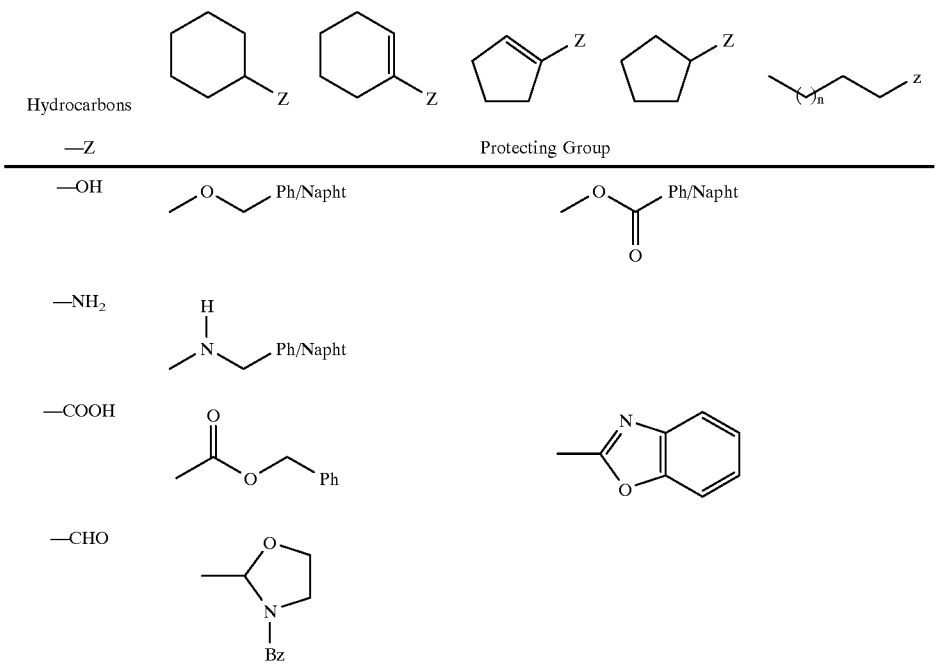

TABLE 1

| | | $K_{app}$ (μM)[a] | |
|---|---|---|---|
| | | WT | Y96A |
| 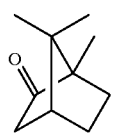 | 1 | 6.3 | 12 |
| 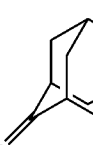 | 2 | 12 | 28 |
|  | 3 | 8.4 | 1.4 |

TABLE 1-continued

| | | $K_{app}$ (μM)[a] | |
|---|---|---|---|
| | | WT | Y96A |
|  | 4 | 330 | 92 |
| 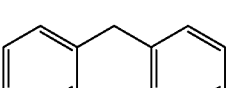 | 5 | >1500[b] | 73 |

[a]Values are the average of two independent measurements using the method of Sligar (S. G. Sligar, Biochemistry, 1976, 15, 5399–5406). The value of $K_{app}$ is strongly dependent on the concentration of $K^+$ in the buffer. At $[K^+]$ > 150 mM. $K_{app}$ for camphor is 0.6 μM for both wildtype and Y96A. Data in this table were determined at $[K^+]$ = 70 mM in phosphate buffer, pH 7.4, in order to avoid salting out of substrates at higher ion concentrations.

[b]Saturation not reached.

TABLE 2(a)

| | | Wild type | | Mutant Y96A | | Wild type | | Mutant Y96A | |
|---|---|---|---|---|---|---|---|---|---|
| P450cam-substrate Interactions Subgroup: 1-ring | | ΔSpin high/low | Vs DTT | ΔSpin high/low | Vs DTT | NADH turnover? | GC? | NADH turnover? | GC? |
|  | Benzene | — | — | — | — | | | | |
| 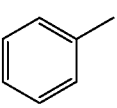 | Toluene | — | — | 30 | 30 | | | | |
| 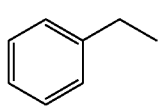 | Ethylbenzene | — | — | 40 | 40 | | | | |
| 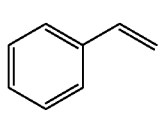 | Styrene | — | — | 30 | 30 | | | | |
|  | Cyclohexene | — | 5 | 40 | 40 | | | | |
|  | 1,3-Cyclohexadiene | nd | nd | nd | nd | | | | |

TABLE 2(a)-continued

| P450cam-substrate Interactions Subgroup: 1-ring | | Wild type ΔSpin high/low | Vs DTT | Mutant Y96A ΔSpin high/low | Vs DTT | Wild type NADH turnover? | GC? | Mutant Y96A NADH turnover? | GC? |
|---|---|---|---|---|---|---|---|---|---|
| | 1,4-Cyclohexadiene | — | 5 | 15 | 20 | | | | |
| | Cyclohexane | — | — | 60 | 60 | | | + | |
| | Hexane | — | — | 70 | 60 | | | + | |
| | Methylcyclohexane | — | — | 70 | 60 | | | | |
| | (S)-(+)-Carvone | 10 | 60 | 10 | 80 | | | | |

TABLE 2(b)

| P450cam-substrate interactions Subgroup: 2-ring, Naphthalene | | Wild type ΔSpin high/low | Vs DTT | Mutant Y96A ΔSpin high/low | Vs DTT | Wild type NADH turnover? | GC? | Mutant Y96A NADH turnover? | GC? |
|---|---|---|---|---|---|---|---|---|---|
| | Naphthalene | — | — | 15 | 20 | | | | |
| | 1-Ethylnaphthalene | — | — | 5 | 20 | | | | |
| | 2-Ethylnaphthalene | — | — | 10 | 20 | | | | |
| | 2-Naphthylacetate | — | 5 | — | 5 | | | | |

TABLE 2(b)-continued

| P450cam-substrate interactions Subgroup: 2-ring, Naphthalene | | Wild type ΔSpin high/low | Wild type Vs DTT | Mutant Y96A ΔSpin high/low | Mutant Y96A Vs DTT | Wild type NADH turn-over? | Wild type GC? | Mutant Y96A NADH turn-over? | Mutant Y96A GC? |
|---|---|---|---|---|---|---|---|---|---|
| | 1-Naphthylacetate | — | 5 | — | 5 | | | | |
| | 1-Naphthylpropionate | — | 20 | 0 | 20 | | | | |
| | 1-Naphthylbutyrate | — | 5 | — | 5 | | | | |
| | Naphthylphenylketone | — | 5 | — | 5 | | | | |
| | 1,2-Dihydronaphthalene | 5 | 20 | 30 | 90 | | | | |
| | 1,2,3,4-Tetrahydro naphthalene | 5 | 10 | 40 | 40 | | | | |

TABLE 2(c)

| P450cam-substrate interactions Subgroup: 2-ring, DPM | | Wild type ΔSpin high/low | Wild type Vs DTT | Mutant Y96A ΔSpin high/low | Mutant Y96A Vs DTT | Wild type NADH turn-over? | Wild type GC? | Mutant Y96A NADH turn-over? | Mutant Y96A GC? |
|---|---|---|---|---|---|---|---|---|---|
| | Diphenylmethane | — | 5 | 45 | nd | | | + | + |

TABLE 2(c)-continued

|  |  | Wild type | | Mutant Y96A | | Wild type | | Mutant Y96A | |
| --- | --- | --- | --- | --- | --- | --- | --- | --- | --- |
| P450cam-substrate interactions Subgroup: 2-ring, DPM |  | ΔSpin high/ low | Vs DTT | ΔSpin high/ low | Vs DTT | NADH turn- over? | GC? | NADH turn- over? | GC? |
|  | Diphenylether | 10 | 5 | 20 | 50 |  |  |  |  |
|  | Benzophenone | — | 20 | — | 20 |  |  |  |  |
|  | Cyclohexylphenylketone | — | 30 | 60 | nd |  |  |  |  |
|  | Phenylbenzoate | — | 5 | — | — |  |  |  |  |
|  | N-Phenylbenzylamine |  | 5 | 45 | nd |  |  |  |  |
|  | Bibenzyl | — | — | 55 | 55 |  |  |  |  |
|  | cis-Stilbene | — | 20 | 40 | 50 |  |  |  |  |
|  | Biphenyl | — | 20 | — | 90 |  |  |  |  |
|  | Cyclohexylbenzene | 20 | 20 | 80 | nd |  |  |  |  |
|  | trans-Stilbene | — | — | — | — |  |  |  |  |

TABLE 2(c)-continued

| P450cam-substrate interactions Subgroup: 2-ring, DPM | | Wild type ΔSpin high/low | Wild type Vs DTT | Mutant Y96A ΔSpin high/low | Mutant Y96A Vs DTT | Wild type NADH turn-over? | Wild type GC? | Mutant Y96A NADH turn-over? | Mutant Y96A GC? |
|---|---|---|---|---|---|---|---|---|---|
| | Benzylether | — | 5 | 55 | nd | | | | |

TABLE 2(d)

| P450cam-substrate interactions Subgroup: 3-ring | | Wild type ΔSpin high/low | Wild type Vs DTT | Mutant Y96A ΔSpin high/low | Mutant Y96A Vs DTT | Wild type NADH turn-over? | Wild type GC? | Mutant Y96A NADH turn-over? | Mutant Y96A GC? |
|---|---|---|---|---|---|---|---|---|---|
| | Anthracene | | | | | | | | |
| | Phenanthrene | — | — | 20 | 20 | | | + | |
| | Fluorene | — | — | — | 50 | | | | |
| | 2-Fluorencarboxzaldehyde | — | — | — | 50 | | | | |
| | 9-Fluorenone | — | 20 | — | 5 | | | | |
| | Anthrone | — | 5 | — | 5 | | | | |
| | Anthraquinone | | | | | | | | |

TABLE 2(d)-continued

| P450cam-substrate interactions Subgroup: 3-ring | | Wild type | | Mutant Y96A | | Wild type | | Mutant Y96A | |
|---|---|---|---|---|---|---|---|---|---|
| | | ΔSpin high/ low | Vs DTT | ΔSpin high/ low | Vs DTT | NADH turn- over? | GC? | NADH turn- over? | GC? |
| [structure] | 2-Ethylanthraquinone | | | | | | | | |

TABLE 2(e)

| P450cam-substrate interactions Subgroup: 4,5-ring | | Wild type | | Mutant Y96A | | Wild type | | Mutant Y96A | |
|---|---|---|---|---|---|---|---|---|---|
| | | ΔSpin high/ low | Vs DTT | ΔSpin high/ low | Vs DTT | NADH turn- over? | GC? | NADH turn- over? | GC? |
| [structure] | Chrysene | — | — | — | — | | | | |
| [structure] | 1,2-Benzanthracene | — | — | — | — | | | | |
| [structure] | Fluoranthene | — | 5 | 20 | 10 | | | | |
| [structure] | Pyrene* | — | — | — | — | | | | |
| [structure] | Perylene* | — | — | — | — | | | | |

TABLE 2(f)

| P450cam-substrate interactions Subgroup: Cyclic Alkanes | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turn-over? | GC? | NADH turn-over? | GC? |
| 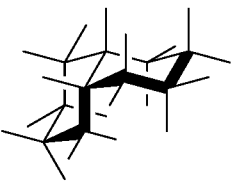 | cis-Decahydro-naphthalene | nd | nd | nd | nd | | | | |
| 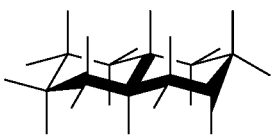 | trans-Decahydro naphthalene | 20 | 10 | 90 | 70 | | | | |
|  | Cyclohexane | — | — | 60 | 60 | | | + | |
| 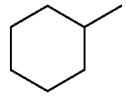 | Methylcyclohexane | 50 | 50 | 100 | 70 | | | | |

TABLE 2(g)

| | | Wild type | | Mutant Y96A | | Wild type | | Mutant Y96A | |
|---|---|---|---|---|---|---|---|---|---|
| P450cam-substrate interactions Subgroup: n-Alkanes | | ΔSpin high/low | Vs DTT | ΔSpin high/low | Vs DTT | NADH turn-over? | GC? | NADH turn-over? | GC? |
| | n-Pentane | — | 5 | 55 | 40 | | | + | |
| | n-Hexane | — | — | 60 | 40 | | | + | |
| | n-Heptane | 5 | 5 | 60 | 40 | | | + | |
| | n-Octane | — | 5 | 80 | 45 | | | + | |
| | n-Nonane | — | — | 70 | 45 | | | + | |
| | n-Decane | nd | nd | nd | nd | | | | |
| | n-Undecane | nd | nd | 20 | 20 | | | | |
| | n-Dodecane | nd | nd | 5 | 5 | | | | |
| $CH_3(CH_2)_{14}CH_3$ | n-Hexadecane | — | — | — | — | | | | |
| $CH_3(CH_2)_{15}CH_3$ | n-Heptadecane | — | — | — | — | | | | |
| $CH_3(CH_2)_{11}OSO_3,Na$ | SDS | — | 20 | — | 60 | | | | |
| $CH_3(CH_2)_7CH=CH(CH_2)_7CO_2H$ | Oleic acid* | — | 10? | — | 20? | | | | |
| $[(CH_3)_2CH(CH_2)_3CH(CH_3)(CH_2)_3CH(CH_3)CH_2CH_2-]_2$ | Squalene | — | — | — | 20 | | | | |
| 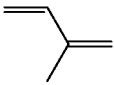 | Isoprene | — | — | 10 | 10 | | | | |

TABLE 2(h)

| P450cam-substrate interactions Subgroup: Camphor-like | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 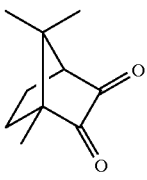 | (1R)-(−)-Camphorquinone | 80 | 80 | 80 | 80 | | | | |
| 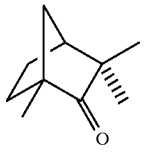 | (1R)-(−)-Fenchone | 40 | 70 | 50 | 80 | | | | |
| 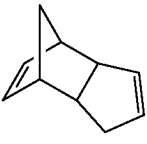 | Dicyclopentadiene | 50 | 80 | 90 | 90 | | | | |

TABLE 3

Turnover of Small Alkanes by P450cam Mutants
All mutants listed below also contain the C334A mutation.
Turnover rate measured as NADH consumption rate
(nmole NADH/nmole P450cam/s).

Alkane substrate:

| Main chain length | Name | Wild type | Y96A |
|---|---|---|---|
| C4 | n-butane | — | — |
| C4 | 2-methyl butane | background | 4.6 |
| C4 | 2,3-dimethyl butane | background | 16.8 |
| C4 | 2,2-dimethyl butane | background | 14.0 |
| C5 | n-pentane | background | 5.8 |
| C5 | 2-methyl pentane | 3.8 | 11.7 |
| C5 | 3-methyl pentane | 1.3 | 14.2 |
| C5 | 2,4-dimethyl pentane | 0.2 | 12.6 |
| C5 | 2,2-dimethyl pentane | 5.2 | 12.8 |
| C5 | 2,2,4-trimethyl pentane | 0.9 | 5.3 |
| C5 | 3-ethyl pentane | background | 16.2 |
| C6 | n-hexane | background | 6.0 |
| C6 | 2-methyl hexane | background | 10.6 |
| C7 | n-heptane | 2.7 | 4.4 |
| C7 | 2-methyl heptane | background | 2.1 |
| C7 | 4-methyl heptane | 1.4 | 10.2 |
| C8 | n-octane | background | 5.8 |
| C7 | cycloheptane | 4.4 | 42.5 |

Product structures and distributions following oxidation of substrates with P450cam active site mutants.
"background" - typical background NADH oxidation rate is 0.07 nmole NADH (nmole P450cam)$^{-1}$ sec$^{-1}$ TABLE 4(a)

Product structure and distributions following oxidation of substrates with P450cam active site mutants. All mutants shown below also contain the C334A mutation.

| Cyclohexylbenzene Products | | | WT | Y96A | Y96F | Y96L | Y96V |
|---|---|---|---|---|---|---|---|
| (D or L, phenyl-cyclohexyl-OH) | D or L | 3-ol | 43 | 20 | 54 | 38 | 28 |
| (L or D, phenyl-cyclohexyl-OH) | L or D | 3-ol | 20 | 20 | 27 | 23 | 39 |
| (Trans-4-ol structure) | | Trans-4-ol | 25 | 15 | 6 | 23 | 10 |
| (Cis-4-ol structure) | | Cis-4-ol | 12 | 45 | 13 | 16 | 23 |
| Total products (area/$10^5$) | | | 0.8 | 7.4 | 1.1 | 10.4 | 12.5 |

Cyclohexylbenzene $\xrightarrow{\text{P450cam}}$

↑ chemically most reactive position

D or L product + additional products

TABLE 4(b)

| Phenylcyclohexene Products | | WT | Y96A |
|---|---|---|---|
| (3-one structure) | 3-one (A) | 24 | 25 |
| (3-ol structure) | 3-ol (B) | 76 | 75 |
| Total products (area/$10^6$) | | 42 | 36 |

Phenylcyclohexene with numbered positions 1–6; chemically reactive positions indicated at positions 2, 3, 5, 6.

$\xrightarrow{\text{P450cam}}$

TABLE 4(b)-continued

| Phenylcyclohexene | Products (%) for mutants: | |
|---|---|---|
| Products | WT | Y96A |

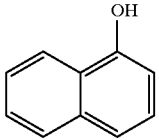

TABLE 4(c)

| Naphthalene Products | | Products (%) for mutants: | | | | | |
|---|---|---|---|---|---|---|---|
| | | WT | Y96A | Y96F | Y96L | Y96V | F87A-F96G-F193A |
| 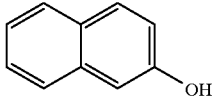 | 1-ol | 100 | 100 | 100 | 100 | 100 | 100 |
| | 2-ol | 0 | 0 | 0 | 0 | 0 | 0 |
| Total products (area/10⁵) | | (0.016) | 1.1 | 2.4 | 0.7 | 1.4 | 0.1 |

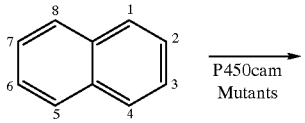

TABLE 4(d)

| Phenanthrene Products | Products (%) for mutants: | | | | | |
|---|---|---|---|---|---|---|
| | WT | Y96A | Y96F | Y96L | Y96V | F87A-F96G-F193A |
| A | 38 | 49 | 41 | 35.5 | 41 | 27 |
| B | 15 | 23 | 31 | 41 | 38 | 41 |
| C | 12 | 13 | 5 | 9 | 11 | 3 |
| D | 35 | 15 | 23 | 14.5 | 10 | 29 |

TABLE 4(d)-continued

| Phenanthrene Products | Products (%) for mutants: | | | | | |
|---|---|---|---|---|---|---|
| | WT | Y96A | Y96F | Y96L | Y96V | F87A-F96G-F193A |
| Total products (area/10⁶) | 0.075 | 7.0 | 4.5 | 2.8 | 1.6 | 0.065 |

Phenanthrene

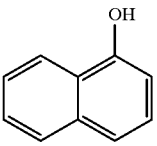

TABLE 4(e)

| Fluoranthene Products | Products (%) for mutants: | | | | | |
|---|---|---|---|---|---|---|
| | WT | Y96A | Y96F | Y96L | Y96V | F87A-F96G-F193A |
| A | 0 | 84 | — | — | — | 0 |
| B | 0 | 16 | — | — | — | 100 |
| Total products (area/10⁶) | 0 | 2.7 | — | — | — | 0.2 |

TABLE 4(e)-continued

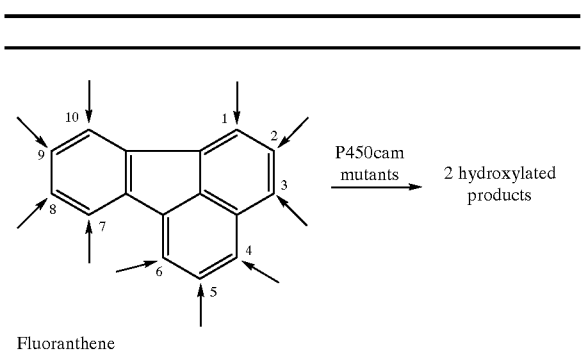

Fluoranthene

TABLE 4(f)

| Pyrene Products | Products (%) for mutants: | | | | |
|---|---|---|---|---|---|
| | WT | Y96A | Y96F | Y96L | Y96V | F87A-F96G-F193A |
| A | 0 | 40 | 43 | 23 | 30 | 33 |
| B | 0 | 43.6 | 29 | 64.5 | 55 | 40 |
| C | 0 | 5 | 12.5 | 7.9 | 12 | 20 |
| D | 0 | 11.4 | 15.5 | 4.6 | 3 | 7 |
| Total products (area/10$^6$) | 0 | 1.2 | 1.5 | 1.5 | 1.6 | 0.02 |

Pyrene

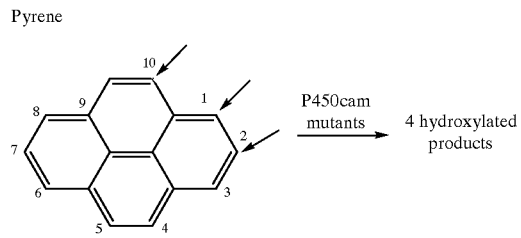

TABLE 4(g)

| Lindane Products (hexachlorocyclohexane) | Products (%) for mutants | |
|---|---|---|
| | WT | Y96A |
| A | 100 | 100 |
| Turnover rate nmole NADH (nmolP450)$^{-1}$s$^{-1}$ | 7.5 | 43.5 |

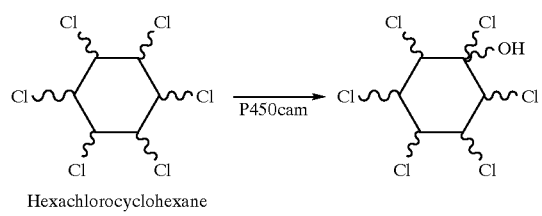

Hexachlorocyclohexane

TABLE 4(h)

| | Products (%) for mutants: | |
|---|---|---|
| | Y96F | Y96A |
| Hexane Products | | |
| 2-hexanone | 10 | 15 |
| 3-hexanone | 16 | 28 |
| 2-hexanol | 24 | 26 |
| 3-hexanol | 50 | 32 |
| Relative activity (WT = 1) | 18.2 | 25.5 |
| 2-Methyl hexane Products | | |
| 2-methyl-2-hexanol | 72 | 74 |
| 5-methyl-2-hexanone | 16 | 14 |
| 2-methyl-3-hexanol | 7 | 4 |
| 5-methyl-2-hexanol | 5 | 8 |
| Relative activity (WT = 1) | 2.3 | 2.6 |

REFERENCES

1. "Cytochrome P-450: Structure, Mechanism, and Biochemistry", ed. P R Ortiz de Montellano, Plenum Press, New York, 1986.
2. T L Poulos, B C Finzel and A J Howard, J. Mol. Biol., 1987, 195, 687–700.
3. J A Peterason, U.-Y. Lu, J Geisselsoder, S Graham-Lorence, C Carmona, F Witney, and M C Lorence, J. Biol. Chem., 1992, 267, 14193–14203.
4. K G Ravichandran, S S Boddupali, C A Hasemann, J A Peterson, and J Deisenhofer, Science, 1993, 261, 731–736.
5. B P Unger, I C Gunsalus, and S G Sligar, J. Biol. Chem., 1986, 261, 1158–1163; J S Miles, A W Munro, B N Rospendowski, W E Smith, J McKnight, and A J Thomson, Biochem. J., 1992, 288, 503–509; T H Richardson, M J Hsu, T Kronbach, H J Barnes, G Chan, M R Waterman, B Kemper, and E F Johnson, Arch. Biochem. Biophys., 1993, 300, 510–516; S S Boddupalli, T Oster, R W Estabrook, and J A Peterson, J Biol. Chem., 1992, 267, 10375–10380; H Li K Darish and T L Poulos, J Biol. Chem., 1991, 266–11909–11914.
6. I C Gunsalus and G C Wagner, Methods Enzymol., 1978, 52, 166–188.
7. P J Goodford, J Med. Chem., 1985, 28, 849–857.
8. Quanta 4.0, Molecular Simulations Inc., 16 New England Executive Park, Burlington, Mass. 01803-5297.
9. J E Baldwin J M Blackburn, R J Heath, and J D Sutherland, Bioorg, Med. Chem. Letts. 1992, 2, 663–668.
10. M J Zoller and M Smith, Nucleic Acids Res., 1982, 10, 6487.
11. T A Kunkel, Proc. Natl. Acad. Sci., 1985, 82, 488–492.
12. C Di Primo, G Hui Bin Hoa, P. Douzou, and S Sligar, J. Biol. Chem., 1990, 265, 5361–5363.
13. D Filipovic, Biochemical and Biophysical Research Communications, Vol. 189, No. 1, 1992, Nov. 30, 1992, pages 488–495.
14. S G Sligar, D Filipovic, and P S Stayton, Methods in Enzymology, Vol. 206, pages 31–49.
15. P J Loida and S G Sligar, Protein Engineering, Vol. 6, No. 2, pages 207–212, 1993.
16. S F Tuck et al., The Journal of Biological Chemistry, Vol. 268, No. 1, Jan. 5, 1993, pages 269–275.
17. W M Atkins and S G Sligar, The Journal of Biological Chemistry, Vol. 263, No. 35, Dec. 15, 1988, pages 18842–18849.

18. W M Atkins and S G Sligar, Biochemistry 1990, 29, 1271–1275.

We claim:

1. A mutant mono-oxygenase cytochrome P-450$_{cam}$ wherein the tyrosine residue at position 96 is replaced by the residue of a small hydrophobic amino acid.

2. The mutant of claim 1, wherein said mutant catalyzes the oxidation of a compound selected from the group consisting of a polycyclic aromatic hydrocarbon, a linear or branched alkane, a biphenyl compound and a halogenated hydrocarbon.

3. The mutant of claim 1, wherein the amino acid is selected from the group consisting of alanine, glycine, isoleucine, leucine, and valine.

4. The mutant of claim 1, wherein an amino acid residue at one or more of the positions 87, 98, 185, 244, 247, 295 or 297 is independently replaced by another amino acid residue.

5. The mutant of claim 2, wherein the amino acid is selected from the group consisting of alanine, glycine, isoleucine, leucine, and valine.

6. The mutant of claim 2, wherein an amino acid residue at one or more of the positions 87, 98, 185, 244, 247, 295 or 297 is independently replaced by another amino acid residue.

7. The mutant of claim 3, wherein an amino acid residue at one or more of the positions 87, 98, 185, 244, 247, 295 or 297 is independently replaced by another amino acid residue.

8. A method of oxidizing a compound selected from the group consisting of a polycyclic aromatic hydrocarbon, a linear or branched alkane, a biphenyl compound or a halogenated variant thereof and a halogenated hydrocarbon, comprising the step of contacting said compound under oxidizing conditions with mono-oxygenase cytochrome P-450$_{cam}$ wherein the tyrosine residue at position 96 is replaced by a small hydrophobic amino acid residue.

9. The method of claim 8, wherein the amino acid is selected from the group consisting of alanine, glycine, isoleucine, leucine, and valine.

10. The method of claim 8, wherein an amino acid residue at one or more of the positions 87, 98, 185, 244, 247, 295 or 297 is independently replaced by another amino acid residue.

11. The method of claim 9, wherein an amino acid residue at one or more of the positions 87, 98, 185, 244, 247, 295 or 297 is independently replaced by another amino acid residue.

* * * * *

UNITED STATES PATENT AND TRADEMARK OFFICE
CERTIFICATE OF CORRECTION

PATENT NO. : 6,100,074
DATED : August 8, 2000
INVENTOR(S) : Sabine Lahja Flitsch; Darren Paul Nickerson; Luet-Lok Wong It is certified that error appears in the above-identified patent and that said Letters Patent is hereby corrected as shown below:

<u>Column 2,</u>
Line 23, "of the" and "in" are deleted.
Line 24, "which" is replaced by -- wherein --, and "and/or the cysteine" is deleted.
Line 25, "residue at position 334" and "any" are deleted.
Line 26, "amino acid except phenylalanine" is deleted.
Lines 28 through 37 are deleted and replaced by the following paragraph:
-- According to another aspect of the present invention, a mutant mono-oxygenase cytochrome P-450cam is provided wherein the tyrosine residue at position 96 is replaced by the residue of a small hydrophobic amino acid, wherein said mutant catalyzes the oxidation of a compound selected from the group consisting of a polycyclic aromatic hydrocarbon, a linear or branched alkane, a biphenyl compound and a halogenated hydrocarbon. --.
Line 41, "diphenyl or" is deleted, and "including" is deleted and replaced by -- or --.
Line 42, "of such a compound or" is deleted and replaced by -- thereof and --.
Lines 43 and 44, "the method comprising contacting the selected one of the compounds" is deleted and replaced by -- comprising the step of contacting the compound --.
Line 45, "in which" is deleted and replaced by -- wherein --.
Lines 46 and 47, "and/or the cysteine residue at position 334 is replaced by another amino acid residue" is deleted and replace by -- is replaced by a small hydrophobic amino acid residue --.

Signed and Sealed this

Thirteenth Day of November, 2001

*Attest:*

NICHOLAS P. GODICI
*Attesting Officer*     *Acting Director of the United States Patent and Trademark Office*